(12) United States Patent
Kasif et al.

(10) Patent No.: US 7,047,137 B1
(45) Date of Patent: May 16, 2006

(54) COMPUTER METHOD AND APPARATUS FOR UNIFORM REPRESENTATION OF GENOME SEQUENCES

(75) Inventors: Simon Kasif, Newton, MA (US); Beth T. Logan, Somerville, MA (US); Pedro J. Moreno, Cambridge, MA (US); Baris Suzek, Baltimore, MD (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 185 days.

(21) Appl. No.: 09/724,269

(22) Filed: Nov. 28, 2000

(51) Int. Cl.
 *G06F 19/00* (2006.01)
 *G01N 33/48* (2006.01)
 *C12Q 1/68* (2006.01)

(52) U.S. Cl. .............................. 702/20; 702/19; 435/6; 707/102; 536/23.1

(58) Field of Classification Search ............ 702/19–29; 707/4, 3, 100, 101, 102; 435/6
 See application file for complete search history.

(56) References Cited

U.S. PATENT DOCUMENTS

| | | | |
|---|---|---|---|
| 6,453,245 B1 * | 9/2002 | Rothberg et al. .............. | 702/20 |
| 6,834,239 B1 * | 12/2004 | Lobanov et al. ............... | 702/22 |
| 6,882,990 B1 * | 4/2005 | Barnhill et al. ................ | 706/16 |
| 6,904,423 B1 * | 6/2005 | Nicolaou et al. .............. | 706/46 |
| 2002/0177138 A1 * | 11/2002 | Boissy ........................... | 435/6 |

OTHER PUBLICATIONS

Levy et al. "Xlandscape: The graphical display of word frequencies in sequences". Bioinformatics, 1998, vol. 14, No. 1, pp. 74-80.*
Jaakkola et al. "Using the Fisher Kernel Method to Detect Remote Protein Homologies". Proceedings of the 7th International Conference on Intelligent Systems for Molecular Biology (ISBM-99), Heidelberg, GER, pp. 149-158 (1999).*
Burges, C.J.C. "A Tutorial of Support Vector Machines for Pattern Recognition". Data Mining and Knowledge Discovery Journal, vol. 2, No. 2, pp. 121-167 (1998).*
Berry et al. Matrices, Vector Spaces and Information Retireval. (Apr. 23, 1999) Society for Industrial and Applied Mathematics Review. 41:2 335-362.*
Stuart et al. A comprehensive vertebrate phylogeny using vector representations of protein sequences from whole genomes. Molecular Biology and Evolution. Apr. 2002, vol. 19 :4 554-562.*
Akutsu, T. Substructure Search and Alignment Algorithms for Three dimensional Protein Structures. Joho Shori Gakkai Kenkyu Hokoku, (1994) vol. 94, No. 82(AL. 41), pp. 1-8.*
Stuart et al. Integrated gene and species phylogenies from unaligned whole genome protein sequences. Bioinformatics. (Jan. 2002) vol. 18 (1) pp. 100-108.*
Akutsu et al. Rapid protein fragment search using hash functions based on the fourier transform. CABIOS (1997) vol. 13: 4 pp. 357-364.*
Altschul, S. F., et al., "Basic Local Alignment Search Tool," *J. Mol. Biol.*, 215:403-410 (1990).
Sonnhammer, E. L. L., "Pfam: A Comprehensive Database of Protein Domain Families Based on Seed Alignments," *Proteins: Structure, Function, and Genetics*, 28:405-420 (1997).
Krogh, A., et al., "Hidden Markov Models in Computational Biology: Applications to Protein Modeling," *J. of Molecular Biology*, 235:1501-1531 (1994).
Human Genome Program, U.S. Department of Energy, "Primer on Molecular Genetics", Washington, D.C., 1992.
Henikoff, S., and Henikoff, J. G., "Automated Assembly of Protein Blocks for Database Searching," *Nucleic Acids Research*, 19(23) :6565-6572 (1991).

* cited by examiner

*Primary Examiner*—Mary K. Zeman
(74) *Attorney, Agent, or Firm*—Richard P. Lange

(57) ABSTRACT

A method and apparatus transforms typically differing length text string representations (i.e., sequences) of biological fragments into uniform length representations. A comparison database stores a predefined number of known biological sequences. A comparison routine compares and scores a subject sequence against each known sequence in the database. Each individual score (one for each known sequence in the database) serves as a vector element forming a fixed length vector representation of the subject sequence. Vector length equals the predefined number of known biological sequences in the database. Scoring is a probability or an occurrence count of the known biological sequence in the subject sequence.

17 Claims, 3 Drawing Sheets

COMPUTER METHOD AND APPARATUS FOR UNIFORM REPRESENTATION OF GENOME SEQUENCES

BACKGROUND OF THE INVENTION

Computational methods for biological sequence analysis are playing an increasingly important role in biology and medicine. The key question addressed by these methods is the discovery of the function of a protein or gene. It is well known that the function of a protein is dictated by its amino acid sequence since this determines the structure of the protein and thus its interaction with the environment.

Proteins are the building blocks of life, supporting a variety of functions which are essential for cell life. These include protection from infections or cancers, gene regulation, survival in different conditions, growth, differentiation, regeneration and others. In fact, the function of every cell in a living organism (whether microbial or human) is determined by which proteins (genes) are expressed in the cell and how they interact in the particular cell environment.

The area of protein function is particularly timely because the new technology of high-throughput genomics generates thousands of hypothetical genes that have not been assigned a putative function. There are numerous commercial applications. Classifying new genes into categories opens many opportunities for new medical treatments. Genes are often used as drugs directly (e.g., insulin), or drug targets (e.g., attacking a particular gene in a microbial organism). Other applications include the design of pesticides, design of new crops, gene therapies and rational drug design.

Proteins are macromolecules found in living organisms which play many roles essential to sustaining life (e.g., forming the physical framework of the organism, acting as enzymes to (promote chemical reactions). A protein is composed of a sequence of several hundred amino acids. Proteins are created in living cells by translating the coding regions (genes) of the DNA sequence. Different proteins are expressed in different cells. The level of expression of different proteins determines the cell function. Since proteins are long and linear complex molecules, they "fold" to give a 3D shape. Biologists have identified four levels of structure which can influence the protein's function:

1. Primary structure—the sequence of amino acids
2. Secondary structure—the presence or absence of small "sub-folds".
   These are regular patterns formed by local folding of the protein (e.g., helices and sheets).
3. Tertiary structure—the final 3D shape
4. Quaternary structure—complexes formed with other proteins.

Given one level of structure, it is not necessarily a trivial task to predict the next level. Hence, function prediction from the primary structure alone is difficult. Therefore, techniques other than sequencing are needed to determine the 3D structure and ultimately the protein function.

The traditional and still most reliable way to perform protein structure prediction is to use laboratory-based techniques such as X-ray crystallography. However, recent years have seen the development of software-based solutions. One such technique is to use dynamic programming-based alignment tools such as "BLAST" to match the new sequence to previously labeled protein sequences (Altshul et al., 1990, Basic Local Alignment Search Tool, JMB 215:403–410). Alternatively, statistical techniques such as Hidden Markov Models (HMM's) can be used to build a model for each labeled class (E. Sonnhammer, S. Eddy and R. Durbin, "Pfam: A Comprehensive Database of Protein Families Based on Seed Alignments," *Proteins*, 1997, pages 405–420). (A. Krogh, M. Brown, I. Mian, K. Sjolander and D. Haussler, "Hidden Markov Models in Computational Biology: Applications to Protein Modeling", *J. of Molecular Biology*, 1994, Volume 235, 1501–1531.) Still another alternative is to learn the boundaries between protein classes rather than a model for the class itself. (Jaakkola, Diekhans, Haussler, "Using the Fisher kernel method to detect remote protein homologies," in Proceedings of ISBM '99). The first two approaches use the protein sequence itself directly to perform classification. The last one uses a HMM to compute the gradient of the protein being produced by the HMM with respect to each of the parameters of the HMM. In summary, none of these methods uses the sensitivity of parts of the protein to motifs to build a feature vector.

Lab-based techniques, such as X-ray crystallography, are expensive and time-consuming. In addition, X-ray crystallography relies on having relatively large amounts of the protein. It cannot work with just a primary description of the protein (i.e., the sequence of amino acids in a file). Finally, it is not possible to crystallize certain proteins in any case (e.g., membrane spanning proteins).

BLAST and other dynamic programming methods are more time-consuming and less accurate than statistical-based techniques.

SUMMARY OF THE INVENTION

The invention addresses the problem of classifying, clustering or indexing proteins and other biological sequences such as genes by using an alternative representation based on high dimensional vectors. Each of the components of the vector represents the sensitivity of the protein (or sequence) to a particular biological motif (described later). Once obtained, this new representation can be used in conjunction with many existing machine learning techniques to analyze the sequences of interest. For example, this new representation may be combined with discriminative classification methods to classify new proteins from the amino acid sequence alone.

The following discloses a new representation of proteins (genes) as objects in a very high-dimensional vector space. This representation offers numerous opportunities for predictive analysis of the space of biological sequences in a novel fashion deploying high-dimensional analysis techniques. The representation relies on aligning very short motif elements (biological templates) to the protein sequence. Subsequently, each protein is encoded as a multi-dimensional vector X, where dimension $X_i$ corresponds to the score obtained by obtaining the maximum score of scoring (convolving) element $E_i$ "against" the protein. The representation allows the use of existing templates (motifs) or to "train" new ones.

For example, currently, limited databases exist which contain protein domain sequences (primary structure) annotated with their secondary and tertiary structure. A protein domain is a subsequence of interest found in proteins. One use of the present invention is to use this labeled data to build models for known protein structures, and then to automatically annotate new proteins according to the models. However, the general idea of the invention may also apply to other protein or gene classification problems and to cluster or index biological sequences.

In a preferred embodiment, a method and apparatus transforms typically differing length text string representations (i.e., sequences) of biological fragments into uniform length representations. A comparison database stores a predefined number of known biological sequences. A comparison routine compares and scores a subject sequence against each known sequence in the database. Each individual score (one for each known sequence in the database) serves as a vector element forming a fixed length vector representation of the subject sequence. Vector length equals the predefined number of known biological sequences in the database. Scoring is by a counting of the number of times the known biological sequence is found in the subject sequence, or the probability of the subject sequence being generated by the known biological sequence.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
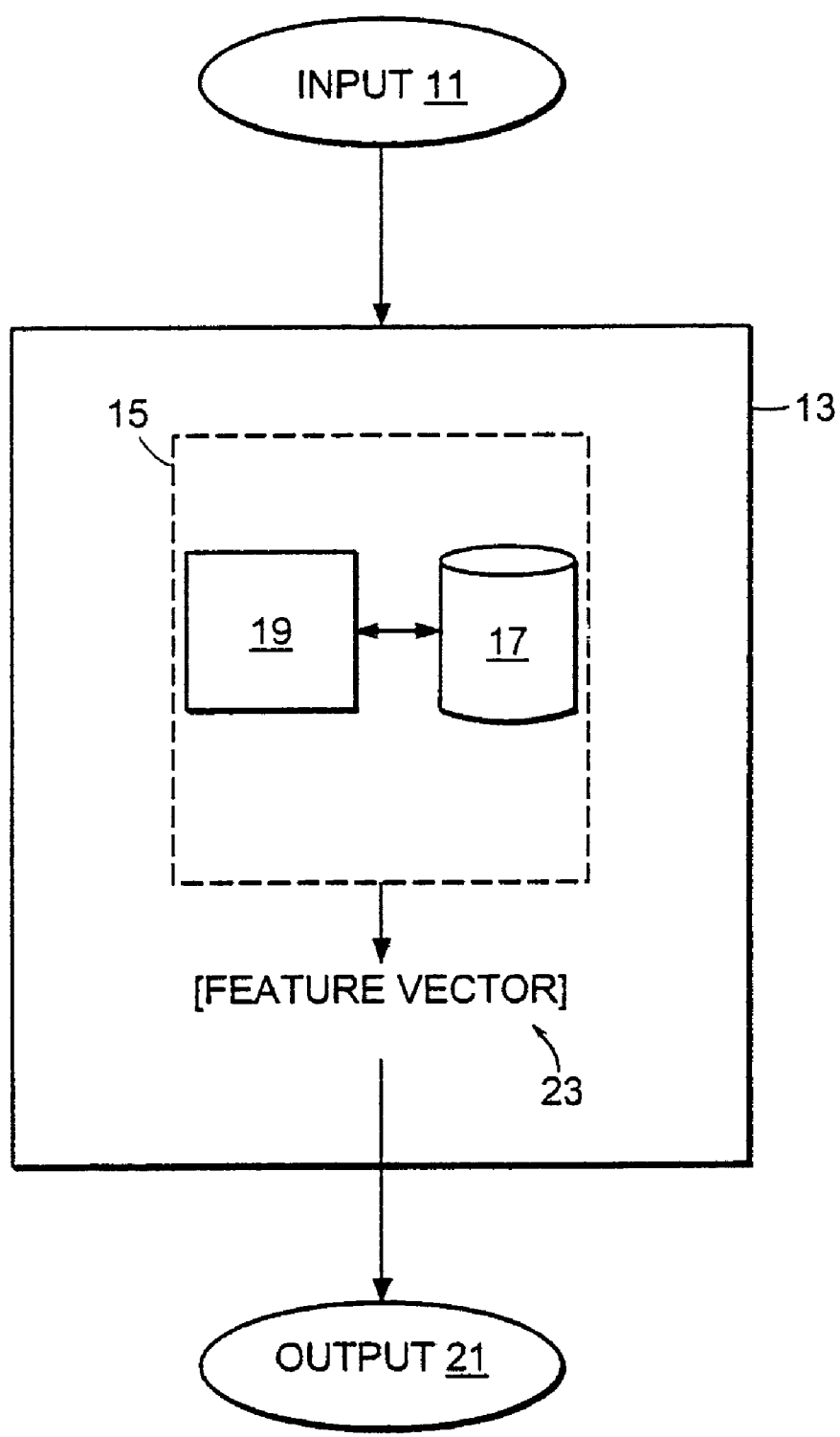
FIG. 1 is a block diagram of a computer implementation of the present invention.

By way of overview, a cell has an operational center called the nucleus which contains structures called chromosomes. Chemically, chromosomes are formed of deoxyribonucleic acid (DNA) and associated protein molecules. Structurally, each chromosome has tens of thousands of genes. Some genes are referred to as "encoding" (or carrying information for constructing) proteins which are essential in the structuring, functioning and regulating of cells, tissues and organs. Thus, for each organism, the components of the DNA molecules encode all the information necessary for creating and maintaining life of the organism. See Human Genome Program, U.S. Department of Energy, "Primer on Molecular Genetics", Washington, D.C., 1992.

The shape of a DNA molecule can be thought of as a twisted ladder. That is, the DNA molecule is formed of two parallel side strands of sugar and phosphate molecules connected by orthogonal/cross pieces (rungs) of nitrogen-containing chemicals called bases. Each long side strand is formed of a particular series of units called nucleotides. Each nucleotide comprises one sugar, one phosphate and a nitrogenous base. The order of the bases in this series (the side strands series of nucleotides) is called the DNA sequence.

Each rung forms a relatively weak bond between respective bases, one on each side strand. The term "base pairs" refers to the bases at opposite ends of a rung, with one base being on one side strand of the DNA molecule and the other base being on the second side strand of the DNA molecule. Genome size or sequence length is typically stated in terms of number of base pairs.

There are four different bases present in DNA: adenine (A), thymine (T), cytosine (C) and guanine (G). Adenine will pair only with thymine (an A-T pair) and cytosine will pair only with guanine (a C-G pair). A DNA sequence is represented in writing using A's, C's, T's and G's (respective abbreviations for the bases) in corresponding series or character strings. That is, the ACTG's are written in the order of the nucleotides of the subject DNA molecule.

As previously mentioned, each DNA molecule contains many genes. A gene is a specific sequence of nucleotide bases. These sequences carry the information required for constructing proteins. A protein is a large molecule formed of one or more chains of amino acids in a specific order. Order is determined by base sequence of nucleotides in the gene coding for the protein. Each protein has a unique function. In a DNA molecule, there are protein-coding sequences (genes) called "exons"; and non-coding-function sequences called "introns" interspersed within many genes. The balance of DNA sequences in the genome are other non-coding regions or intergenic regions.

According to the foregoing method of representing genome and DNA sequences, the DNA sequence specifies the genetic instructions required to create a particular organism with its own unique traits and at the same time provides a text (character string) environment in which to study the same.

Illustrated in FIG. 1 is a computer system embodying the present invention. A digital processor 13 executes invention software program 15 in working memory. The invention software program 15 receives as input 11 a subject amino acid (i.e., protein or DNA) sequence or subsequence. The input sequence/subsequence 11 is a text string (consisting of A's, C's, T's, and G's) for representing the sequence of amino acids. Each amino acid can be represented by one or more characters, an example of which is given in Table 1.

TABLE 1

| Amino Acid | 3-Letter Code | 1-Letter Code |
| --- | --- | --- |
| Alanine | Ala | A |
| Cysteine | Cys | C |
| Aspartate | Asp | D |
| Glutamate | Glu | E |
| Phenylalanine | Phe | F |
| Glycine | Gly | G |
| Histidine | His | H |
| Isoleucine | Ile | I |
| Lysine | Lys | K |
| Leucine | Leu | L |
| Methionine | Met | M |
| Asparagine | Asn | N |
| Proline | Pro | P |
| Glutamine | Gln | Q |
| Arginine | Arg | R |
| Serine | Ser | S |
| Threonine | The | T |
| Valine | Val | V |
| Tryptophan | Trp | W |
| Tyrosine | Tyr | X |

Different amino acid sequences have different length text string representations. Hence, the input sequences to invention program 15 are of varying lengths. Using a predefined set 17 of known biological fragments, the invention software program 15 performs a comparison routine 19 against the subject amino acid sequence input 11. The comparison routine 19 effectively transforms the traditional text representation of the subject amino acid sequence 11 into a fixed length vector 23. That is, the comparison routine 19 transforms the input sequences of varying length into respective same length (i.e., uniform length) feature vectors 23.

In the preferred embodiment, the number of known biological fragments in the predefined set 17 defines the length of resulting feature vectors 23.

The output 21 of the invention software 15 (i.e., normalized representations of amino acid sequences, each representation being of the same length) may then be fed into analyses of typical interest in biotechnology. Such analyses include classification, clustering and indexing.

It is understood that input amino acid sequences 11 may be received from input devices (e.g., a keyboard, mouse, etc.), another computer coupled across a communication channel to digital processor 13 (i.e., in a local area, wide area and/or global/Internet network), and the like. Similarly, output 21 of the uniform length feature vectors 23 of the invention software 15 may be transmitted to a data file/data store, another program/processor routine, another computer coupled across a communication channel to digital processor 13, and the like.

Figure 2:
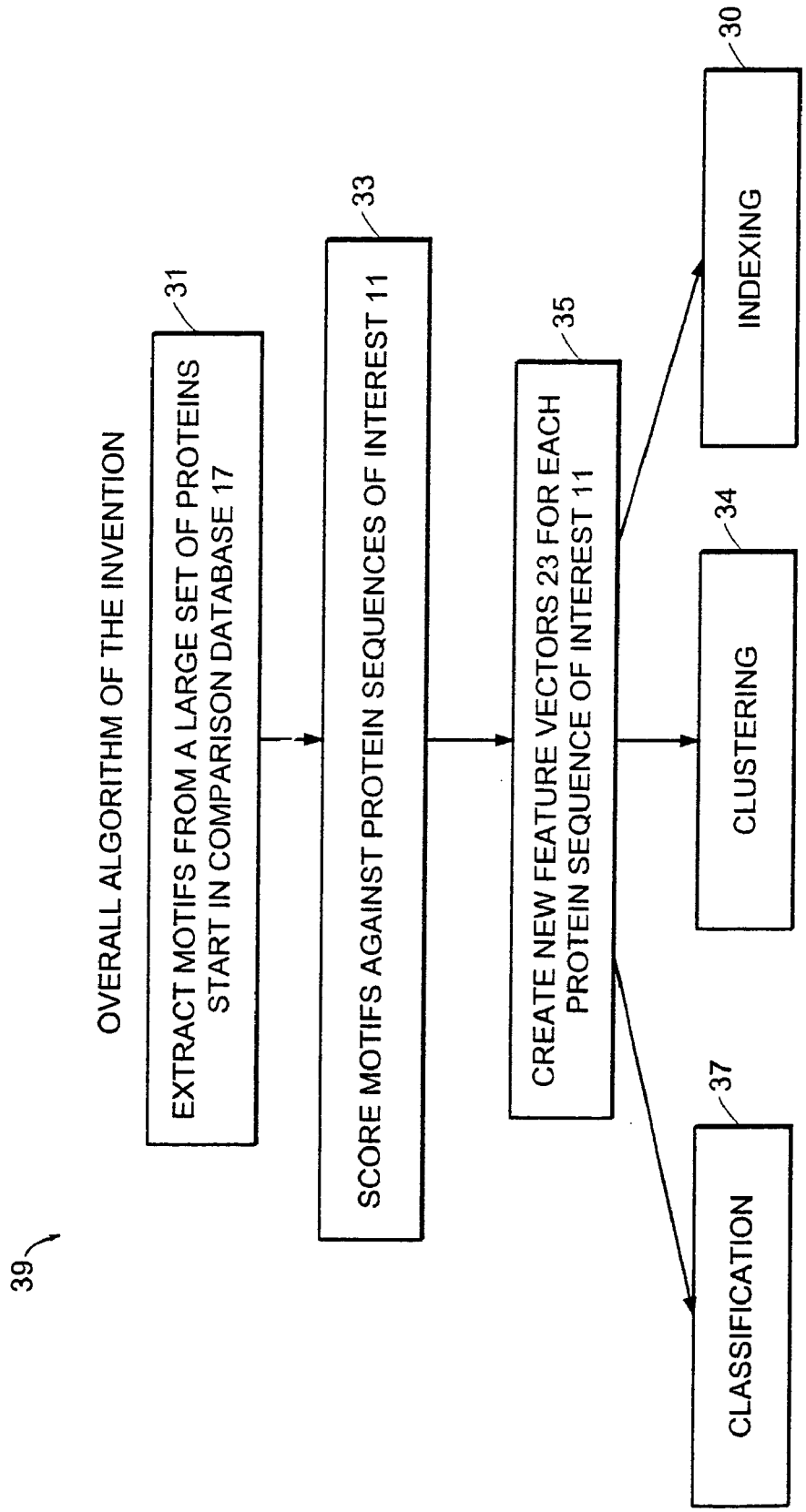
FIG. 2 is a flow diagram of the present invention overall process.
Figure 3:
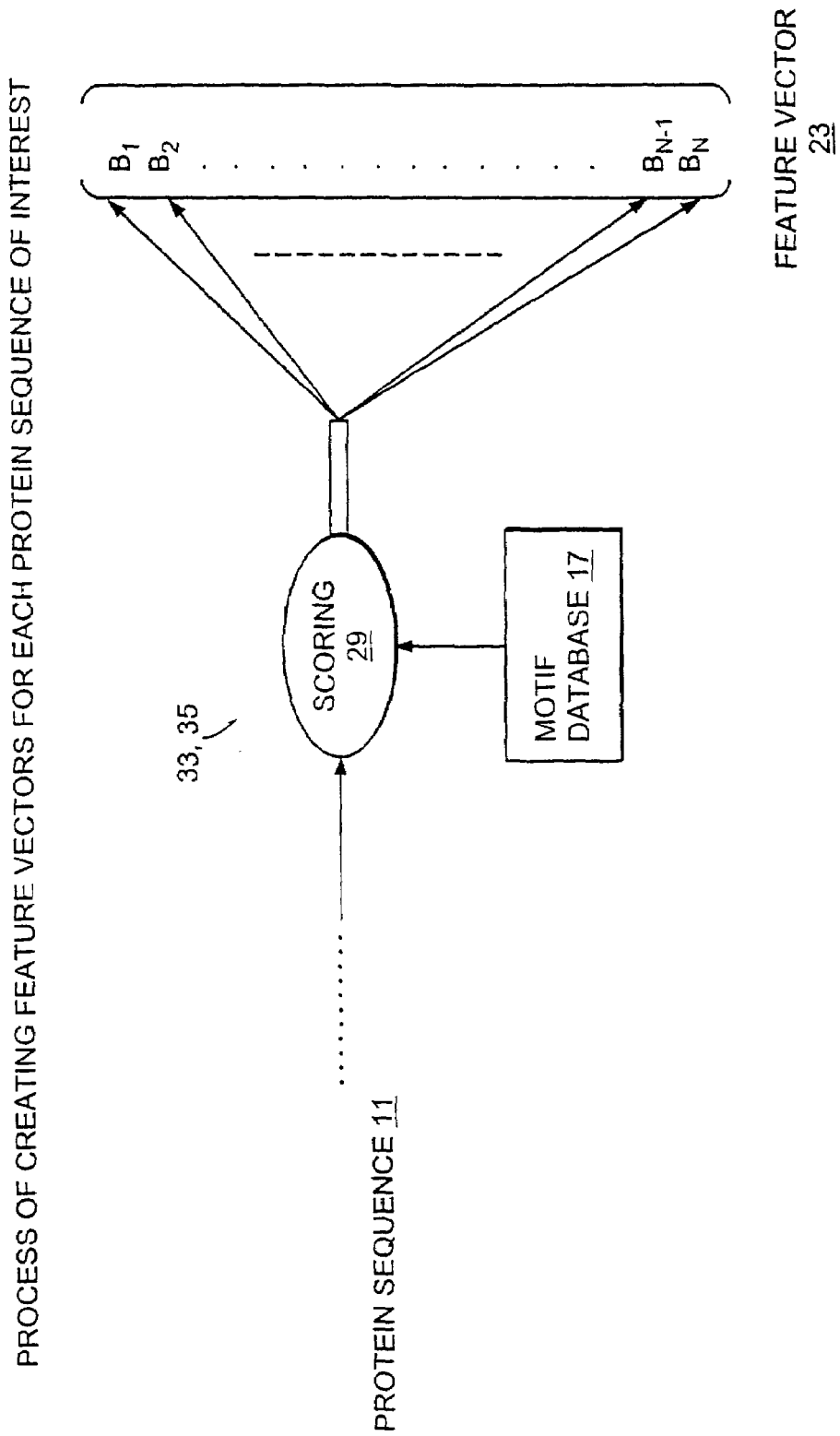
FIG. 3 is a schematic of the invention transform into feature vectors utilized in the overall process of FIG. 2.

Accordingly, the present invention method provides a two-step process 39. First, the invention method converts the amino acid sequences 11 of interest to high dimensional feature vectors 23. Once this transformation has taken place, then one may apply any number of statistical learning techniques to train models for classification, clustering or indexing the protein sequences in the second step of the overall invention process 39. FIGS. 2 and 3 describe these steps as detailed below. Although this description, details the overall process 39 as it applies to the analysis of protein sequences or subsequences, it is understood that invention method and techniques may also be applied to DNA sequences or subsequences.

The first half/phase of the invention method/process 39 illustrated in FIG. 2 converts each protein sequence or subsequence of interest 11 to a new representation of fixed length, i.e., any protein sequence no matter now long it is, is converted into a feature vector 23 of fixed length. Preferably each dimension of these feature vectors 23 represents the sensitivity of the protein to a particular biological motif. Therefore, in order to create feature vectors 23, the invention method first creates or obtains a comparison database 17 of short, highly conserved regions in related protein domains (step 31). Such regions are often called "blocks", "motifs" or "probabilistic templates".

A working motif is preferably represented by a K by L matrix M in which each of the K rows represents a particular amino acid (or nucleotide for DNA sequences) and L represents the length of the motif. For protein sequences, K=20. For DNA sequences K=4. Each cell, as indicated by [amino acid, position in the length], in the matrix M holds a value that represents the probability of that amino acid existing in that position. This matrix may alternatively store log-ratios rather than probabilities. Thus, a motif may be thought of as a 0-th order Markov model.

The BLOCKS database (Steven Henikoff and Jorja G. Henikoff, "Automated assembly of protein blocks for database searching," *Nucleic Acids Research*, 19:23, pp. 6565–6572 (1991)) is an example of a database 17 of motifs. Emitof, and PRINTs are other such databases. These and other published databases may be used as the working predefined set/comparison database 17 in the present invention. Alternatively, it is possible to create a new motif database 17 from any protein database which has been labeled according to some parameter (e.g., structure). This is achieved by using multiple alignment software to find short multiply aligned ungapped sequences and then collecting statistics about these in a matrix. By creating a motif database 17 specific to the proteins of interest 11, more meaningful feature vectors 23 may be obtained since the motifs from a more general database may not occur in the proteins of interest.

To create a feature vector 23 for each protein sequence 11 of interest, the invention method at step 33 searches for each motif (generated in step 31 and stored in database 17) in the sequence 11 and scores the search results as a count of number of matches found or as a probability, or the like. In the preferred embodiment, in step 33, each motif of length L is scored against the subject protein sequence 11 by computing the probability of every subsequence of length L in the subject sequence 11 being generated by the model (matrix M discussed above) that corresponds to the motif.

This is illustrated in FIG. 3 where subject protein sequence 11 is shown being scored against each motif in comparison database 17 (obtained from step 31). The score (probability or count, etc.) 29 of a first motif against input sequence 11 is indicated as $B_1$ in FIG. 3. The score of a second motif relative to the same input sequence 11 is indicated as $B_2$ and so on in FIG. 3. The ordered series of individual motif scores $B_i$ is $[B_1 \ldots B_N]$ and represents the feature vector 23 created for subject sequence 11. N is the fixed number of motifs in comparison database 17 that are processed against each input sequence 11 of interest.

Thus, the result at 35 in FIG. 2 is an N-dimensional feature vector where N is the total number of motifs in comparison database 17 as explained above. Each dimension J contains a score describing the degree of alignment of motif J to the subject input sequence 11. For the case where a motif is detected multiple times in input subject sequences 11, the preferred embodiment applies a variety of heuristics at step 35. For example, the invention process 39 takes the maximum of all scores for that block in an input subject sequence 11 or the sum of such scores. In preliminary experiments, Applicants found that taking the maximum score gives superior classification performance. Invention process 39 may also apply a threshold such that scores below a certain number are set to zero at step 35. Additionally, given the complete set of feature vectors 23 for input subject sequences 11, one may (at step 35) reduce the dimensionality of these vectors using standard dimension reduction techniques such as Principal Components Analysis (PCA).

Continuing in FIG. 2, the second phase in invention overall process 39 includes clustering 34, classification 37 and indexing 30 analyses of interest.

Once all the protein sequences or subsequences of interest 11 have been transformed to feature vectors 23, models may be generated to describe these features and perform clustering 34, classification 37 or indexing 39. Each of these analyses is described below.

Clustering 34

A clustering process 34 groups together proteins (subject sequences) 11 with similar feature vectors 23 in order to discover previously unknown relationships between them. For example, using well known algorithms such as k-means or nearest neighbors, it is possible to decide if two proteins 11 as represented by the newly generated feature vectors 23 are close in sequence pattern or not. The key concept here is that the new representation (uniform length feature vector 23) allows subsequent analyses to compare proteins (sequences) both reliably and effectively.

Classification 37

The process of classification 37 attempts to learn a relationship or model given a set of labeled feature vectors 23 called the "training set". Each label denotes the class that the vector 23 belongs to. For example, the classes may be defined by protein structural information. Possibly the labeling is generated by clustering. Given this model, unseen vectors, usually denoted the "testing set", are assigned labels according to the models learned. An example of the classification of proteins into structural classes is described below.

Indexing 30

Indexing 30 organizes a database of protein sequences in such a way that for a given protein (represented by its feature vector 23), "similar" proteins can be found efficiently. One implementation uses the AltaVista index to index a database of proteins as represented by the generated feature vectors 23. A new "query" protein is presented to AltaVista and all similar proteins are retrieved. The similarity function used in AltaVista is modified to correspond to the vector elements of feature vectors 23. Clustering and classification techniques usually form an integral part of indexing algorithms. The main idea here is to use the index to retrieve the most similar proteins to a given query, rather than a single classification into a single structural class. This operation has important applications for biologists who are involved in drug design since a set of similar proteins can suggest multiple possible functions for a given query protein.

EXAMPLE

An example method of classifying subject sequences according to the present invention follows.
1. Given a set of training protein sequences labeled according to structure, convert each of these into a multidimensional feature vector 23 as described above. Utilize the BLOCK's motif database as the comparison database 17 to create the feature vectors 23.
2. Given the labeled feature vectors generated in step 1, learn corresponding Support Vector Machine (SVM) classifiers (Burger, 1998, "A tutorial on Support Vector Machines for Pattern Recognition," *Data Mining and Knowledge Discovery Journal*) to separate each structural class from "the rest of the world". A SVM classifier learns a separating hyperplane between two classes which maximizes the "margin"—the distance between the hyperplane and the nearest datapoint of each class.

The appeal of SVM's is twofold. First, they do not require any complex tuning of parameters, and second they exhibit a great ability to generalize given a small training corpra. They are particularly amenable for learning in high dimensional spaces. The only parameters needed to tune a SVM are the "capacity" and the choice of kernel. The capacity allows one to control how much tolerance for errors in the classification of training samples one allows and therefore the generalization ability of the SVM. A SVM with high capacity will classify all training samples correctly but will not be able to generalize well for testing samples. In effect, it will construct a classifier too tuned for the training samples which will limit its ability to generalize later on when testing samples are presented to the system. Conversely, a very low capacity will produce a classifier that does not fit the data sufficiently accurately. It will allow many training and testing samples to be classified incorrectly.

The second tuning parameter, called the kernel, allows the SVM to create hyperplanes in high dimensional spaces that effectively separate the training data. Often in the input space training vectors cannot be separated by a simple hyperplane. The kernel allows transforming the data from one space to another space where a simple hyperplane can effectively separate the data in two classes.

In step 2, tune these two parameters separately for each structural family of interest.

An additional step consists of tuning the operating point of the classifier so that one may control the amount of false negatives. In one implementation, Applicants find a threshold value such that any score returned by the SVM that is bigger than this guarantees no false negatives.

3. Given a set of unlabeled structural sequences (the input testing set) convert each of these into a corresponding multidimensional feature vector 23 using BLOCKS as above.
4. Now, for each unlabeled feature vector, to determine if it belongs to a particular class, test it using the SVM created for that class. The SVM classifier will produce a "score" representing the distance of the testing feature vector from the margin. The bigger the score the further away the vector is from the margin and the more confident the classifier is in its own output. If the score is below the threshold set in Step 2, classify the vector (and hence the corresponding test input sequence) as belonging to that particular class. Otherwise, it is classified as not belonging to the class. For multi-class classification one may use standing procedures such as classifying based on the highest score returned by each of the individual classifiers.

While this invention has been particularly shown and described with references to preferred embodiments thereof, it will be understood by those skilled in the art that various changes in form and details may be made therein without departing from the scope of the invention encompassed by the appended claims.

For example, the foregoing describes a method and apparatus for transforming representations of protein or DNA sequences and/or subsequences. It is understood that representations of other biological sequences (human or other) may similarly be transformed using the disclosed techniques and methods.

What is claimed is:
1. A method of assigning one or more subject genome sequences to a class, comprising:
(a) providing a set of known biological fragments, the set being of a fixed number of said known biological fragments, each known biological fragment in the set having a respective representation;
(b) providing at least one training sequence;
(c) for each known biological fragment, quantitatively determining a score with respect to each training sequence;
(d) for each training sequence, forming a training feature vector, said training feature vector being a sequence of scores of each known biological fragment with respect to the training sequence;
(e) using the training feature vectors, classifying the training sequences, thereby defining classes of sequences;
(f) providing a subject genome sequence;
(g) quantitatively determining a score of each known biological fragment with respect to the subject genome sequence;
(h) forming a feature vector of the subject genome sequence, said feature vector being a sequence of scores of each known biological fragment in the set; and
(i) using the feature vector and the training feature vectors, assigning the subject genome sequence to at least one of the defined classes of sequences, thereby producing, classification, of the subject genome sequence.

2. A method as claimed in claim 1 wherein the set of known biological fragments is from published databases of motifs or proteins.

3. A method as claimed in claim 1 wherein step (f) includes providing a plurality of subject genome sequences, and step (h) forms a respective feature vector for each subject genome sequence such that each subject genome sequence has a respective vector representation of a same length, said set of known biological fragments being a same set used for all of said subject genome sequences.

4. A method as claimed in claim 1 wherein the subject genome sequence is a DNA sequence or subsequence or protein sequence or subsequence.

5. A method as claimed in claim 1 wherein step (g) quantitatively determining a score includes determining probability of the subject genome sequence being generated by the known biological fragment by (1) counting the number of times the known biological fragment is found in the subject genome sequence and (2) from said counted number of times, forming a vector element, such that for each known biological fragment there is a respective vector element representing the number of times that known biological fragment is found in the subject genome sequence.

6. A method as claimed in claim 5 wherein the counting determining probability employs a 0-th order Markov model for each known biological fragment.

7. The method of claim 1 wherein the respective representation of each known biological fragment is a text string.

8. The method of claim 7 wherein quantitatively determining a score of each known biological fragment in the set includes for each known biological fragment, counting the number of times the text string of the respective representation is found within the subject genome sequence.

9. The method of claim 1 wherein the respective representation of each known biological fragment is a probabilistic template, said template providing a probability that a member of a group consisting of amino acids and nucleotides exists at a pre-determined position of said known biological fragment.

10. The method of claim 9 wherein quantitatively determining a score of each known biological fragment in the set includes for each known biological fragment, computing the probability of existence of every subsequence of a pre-determined length in the subject genome sequence according to the probabilistic template that represents the known biological fragment.

11. Apparatus for assigning a subject genome sequence to a class, comprising:
(1) an input device for inputting at least one subject genome sequence and at least one training sequence;
(2) a data store of representations of a set of a predefined number of known biological fragments; and
(3) a scoring routine executed by a digital processor having access to the data store, the scoring routine quantitatively determining a score of each known biological fragment in the set as compared against the subject genome sequence or each training sequence, said scores forming a feature vector or a training feature vector having a length equal to the predefined number of known biological sequences; and
(4) an analyzing routine executed by a digital processor, the analyzing routine performing the steps of:
(a) using the training feature vectors, classifying the training sequences, thereby defining classes of sequences; and
(b) using the feature vector and the training feature vectors, assigning the subject genome sequence to at least one of the defined classes of sequences, thereby producing classification, of the subject genome sequence,
wherein the digital processor provides the produced classification as output.

12. Apparatus as claimed in claim 11 wherein the data store is a published database of motifs or proteins.

13. Apparatus as claimed in claim 11 wherein the subject genome sequence is a DNA sequence or subsequence or protein sequence or subsequence.

14. The apparatus of claim 11 wherein each known biological fragment in the set is represented by a respective text string.

15. The apparatus of claim 14 wherein the scoring routine includes for each known biological fragment, counting the number of times the respective text string is found within the subject genome sequence.

16. The apparatus of claim 11 wherein each known biological fragment in the set is represented by a probabilistic template, said template providing a probability that a member of a group consisting of amino acids and nucleotides exists at a pre-determined position of said known biological fragment.

17. The apparatus of claim 16 wherein the scoring routine includes for each known biological fragment, computing the probability of existence of every subsequence of a pre-determined length in the subject genome sequence according to the probabilistic template that represents the known biological fragment.

* * * * *